US00PP22155P2

(12) United States Plant Patent
Bergman

(10) Patent No.: US PP22,155 P2
(45) Date of Patent: Sep. 20, 2011

(54) ***CHRYSANTHEMUM* PLANT NAMED 'SYNHONY DURANGO'**

(50) Latin Name: *Chrysanthemum×morifolium*
Varietal Denomination: Synhony Durango

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/803,608

(22) Filed: Jun. 30, 2010

(51) Int. Cl.
*A01H 5/00* (2006.01)

(52) U.S. Cl. ..... Plt./290

(58) Field of Classification Search ..... Plt./290
See application file for complete search history.

*Primary Examiner* — Annette Para
(74) *Attorney, Agent, or Firm* — S. Matthew Edwards

(57) ABSTRACT

A new *Chrysanthemum* plant named 'Synhony Durango' particularly distinguished by the yellow-orange ray floret color, large decorative type semi-double flowers, strong stems, good shelf life, dark green foliage, and about an 8 week flowering response time.

1 Drawing Sheet

Lain name of the genus and species of the plant claimed: *Chrysanthemum×morifolium.*

Varietal denomination: 'Synhony Durango'.

BACKGROUND OF THE NEW PLANT

The present invention comprises a new *Chrysanthemum,* botanically known as *Chrysanthemum×morifolium,* and hereinafter referred to by the variety name 'Synhony Durango'.

'Synhony Durango' is a product of a planned breeding program. The new cultivar has yellow-orange ray floret color, large decorative type semi-double flowers, strong stems, good shelf life, dark green foliage, and about an 8 week flowering response time.

'Synhony Durango' originates as a natural whole plant mutation of 'Yodurango', U.S. Plant Pat. No. 19,736. 'Synhony Durango' was discovered and selected by the inventor as a single flowering plant within a population of the parent cultivar in a field trial in Fort Myers, Fla. in February 2007. The parent cultivar 'Yodurango' has orange-bronze ray floret color.

The first act of asexual reproduction of 'Synhony Durango' was accomplished when vegetative cuttings were propagated from the initial selection in May 2007 in a controlled environment in Fort Myers, Fla.

BRIEF SUMMARY OF INVENTION

Horticultural examination of plants grown from cuttings of the plant initiated in May 2007, and continuing thereafter, has demonstrated that the combination of characteristics as herein disclosed for 'Synhony Durango' are firmly fixed and are retained through successive generations of asexual reproduction.

'Synhony Durango' has not been observed under all possible environmental conditions. The phenotype may vary significantly with variations in environment such as temperature, light intensity and day length.

A Plant Breeder's Right for this cultivar was applied for in Canada on Oct. 30, 2009 (#09-6765). 'Synhony Durango' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Synhony Durango' with colors being as true as possible with an illustration of this type. The photographic drawing shows 4 flowering potted plants of the new variety growing in a 6 inch pot and a close-up of the flowers.

DETAILED BOTANICAL DESCRIPTION

The plant descriptions, measurements and aforementioned photographs were taken in Gilroy, Calif. in April 2010 under natural light. These plants were started and grown in Nipomo, Calif. and were shipped to California in April. Plants were grown under conditions which approximate those generally used in commercial potted chrysanthemum production. These plants used in the photograph and descriptions were about 10 weeks old.

Color references are made to The Royal Horticultural Society Colour Chart (R.H.S.) 2001.

TABLE 1

DIFFERENCES BETWEEN THE NEW VARIETY 'SYNHONY DURANGO' AND A SIMILAR VARIETY

| | 'Synhony Durango' | 'Orange Yochatham' (U.S. Plant Pat. No. 20,495) |
|---|---|---|
| Inflorescence diameter: | Larger | Smaller |
| Ray floret length: | Longer | Shorter |
| Foliage length: | Longer | Shorter |
| Foliage color: | Darker | Lighter |

Plant:
*Form, growth and habit.*—Herbaceous decorative (pot-type). Stems strong, upright and outwardly spreading, good shelf life, suitable for production using disbudded, center budded or no bud removal.
*Plant height.*—19-21 cm.
*Plant height (inflorescence included).*—25-28 cm.
*Plant width.*—36-40 cm.
Roots:
*Number of days to initiate roots.*—4 days at about 22 degrees C.
*Number of days to produce a rooted cutting.*—10 days at 22 degrees C.
*Type.*—Fine, fibrous, free branching.
*Color.*—RHS N155B but whiter.
Foliage:
*Arrangement.*—Alternate.
*Immature, leaf color, upper surface.*—Closest to RHS 147A.
*Lower surface.*—RHS 147B.
*Mature, leaf color, upper surface.*—Lighter than RHS 147A.
*Lower surface.*—RHS 147B.
*Length.*—9.5-10.3 cm.
*Width.*—6.6-7.0 cm.
*Shape.*—Ovate.
*Base shape.*—Attenuate.
*Apex shape.*—Acute to mucronulate.
*Margin.*—Palmately lobed, slightly serrate.
*Texture, upper surface.*—Bi-fid T-shaped hairs.
*Lower surface.*—Bi-fid T-shaped hairs.
*Color of veins, upper surface.*—RHS 147C.
*Color of veins, lower surface.*—RHS 147C.
*Petiole color.*—RHS 147C.
*Length.*—1.5-2.0 cm.
*Diameter.*—0.4-0.5 cm.
*Texture.*—Bi-fid T-shaped hairs.
Stem:
*Quantity of main branches per plant.*—3-4.
*Color of stem.*—RHS 146B but appears lighter being heavily covered with hairs.
*Length of stem.*—19-21 cm.
*Diameter.*—0.5-0.6 cm.
*Length of internodes.*—1.5-2.5 cm.
*Texture.*—Bi-fid T-shaped hairs.
*Color of peduncle.*—RHS 146B but appears lighter being heavily covered with hairs.
*Length of peduncle.*—2.0 cm.
*Peduncle diameter.*—0.4 cm.
*Texture.*—Bi-fid T-shaped hairs.
Inflorescence:
*Type.*—Composite type, solitary inflorescences (decorative-type) borne terminally above foliage, ray florets arranged acropetally on a capitulum, and sometimes twisted.
*Quantity of short days to flowering (response time).*—About 50-54 days.
*Quantity of inflorescences per plant.*—6-9.
*Lastingness of individual blooms on the plant.*—About 21 days.
*Fragrance.*—Slight.
Bud: (Just before opening/showing color)
*Color.*—RHS 2C.
*Length.*—0.7-0.8 cm.
*Width.*—1.0 cm.
*Shape.*—Oblate.
Immature inflorescence:
*Diameter.*—7-8 cm.
*Color of ray florets, upper surface.*—RHS 6A.
*Lower surface.*—RHS 8A.
Mature inflorescence:
*Diameter.*—10-11 cm.
*Depth.*—4.5 cm.
*Total diameter of 'disc'.*—0.5 cm but is hidden by immature ray florets.
*Receptacle height.*—0.5 cm.
*Receptacle diameter.*—1.3 cm.
Ray florets:
*Average quantity of florets.*—About 150 in numerous whorls.
*Color of florets, upper surface.*—RHS 12A overlaid with RHS 14B and RHS 17B; with a reddish hue basally.
*Lower surface.*—RHS 8A to RHS 8B.
*Length.*—5.0-6.0 cm.
*Width.*—1.0-1.3 cm.
*Shape.*—Oblong, somewhat twisted.
*Apex shape.*—Rounded to slightly emarginate.
*Margin.*—Entire.
*Texture, upper surface.*—Papillose.
*Lower surface.*—Papillose.
Disc florets:
*Average quantity of florets.*—About 30.
*Color of florets.*—RHS 1B with RHS 1C basally.
*Length.*—0.5 cm.
*Width.*—0.1 cm.
*Shape.*—Tubular, enlongated.
*Apex shape.*—Acute, 5 pointed.
Phyllaries:
*Quantity.*—About 25-30.
*Color, upper surface.*—Closest to RHS 147A.
*Lower surface.*—Between RHS 147A and RHS 147B.
*Length.*—1.0-1.3 cm.
*Width.*—0.2 cm.
*Shape.*—Lanceolate.
*Apex shape.*—Acute.
*Based.*—Fused.
*Margins.*—Entire, papery.
*Texture, upper surface.*—Glossy, smooth.
*Lower surface.*—Bi-fid T-shaped hairs.
Reproductive organs:
*Found on both florets.*—
*Pistil.*—1.
*Length.*—0.4-0.6 cm.
*Style color.*—RHS 1B but more translucent.
*Style length.*—0.2-0.4 cm.
*Stigma color.*—RHS 5A. Stigma shape: Bi-parted. Ovary color: Not observed.
*Found on only disc florets.*—Stamens: 1. Color of filaments: RHS 1B to RHS 1C but more translucent. Length filaments: 0.2 cm. Anther color: RHS 15B. Anther length: 0.2 cm. Anther shape: Oblong. Color of pollen: RHS 15A. Pollen amount: Poor. Fertility/seed set: Has not been observed on this hybrid.
Disease/pest resistance: Disease/pest resistance has not been observed on this hybrid.

What is claimed is:

1. A new and distinct variety of *Chrysanthemum* plant named 'Synhony Durango' substantially as illustrated and described herein.

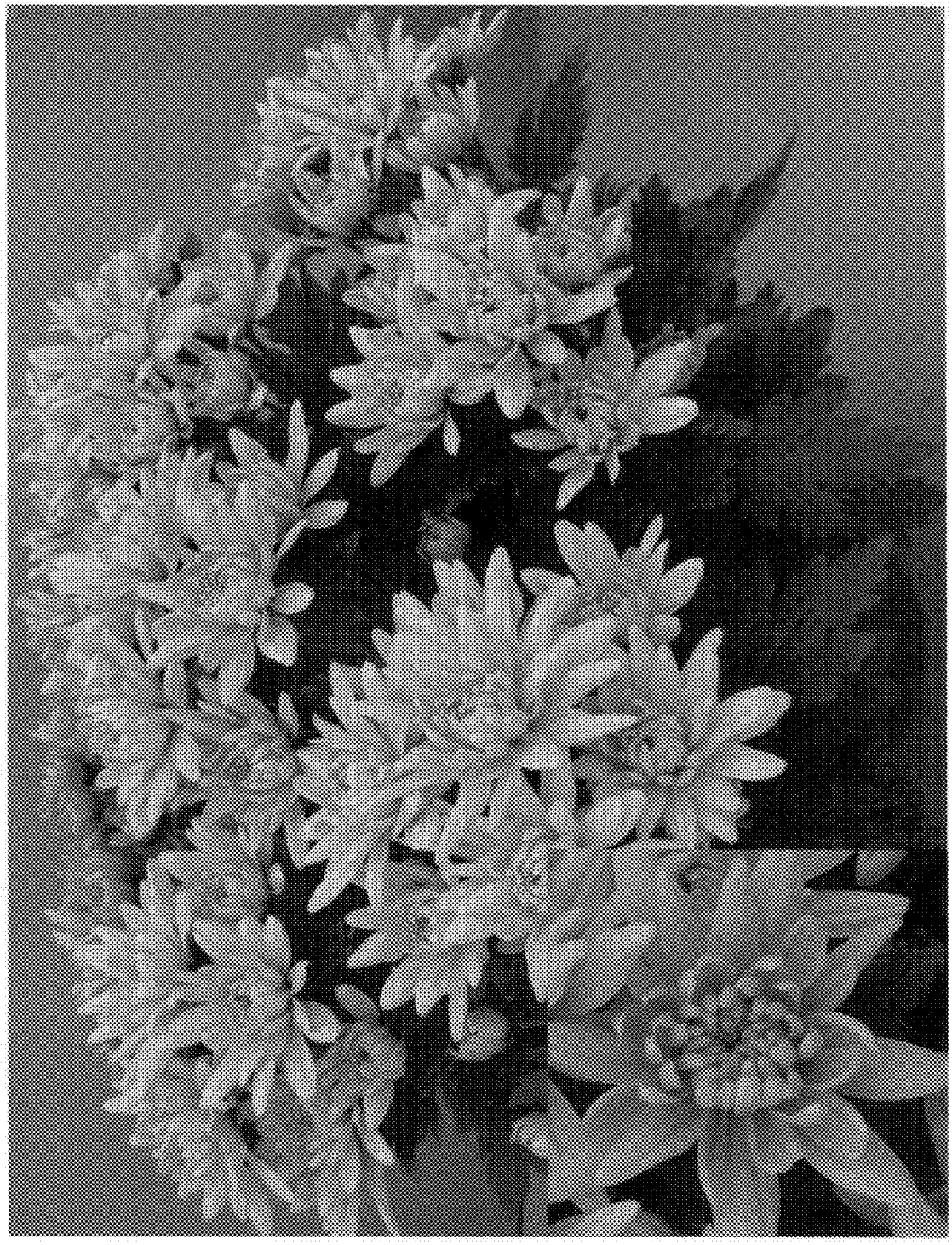

* * * * *